United States Patent [19]
Gilblom

[11] Patent Number: 6,151,382
[45] Date of Patent: Nov. 21, 2000

[54] X-RAY IMAGING APPARATUS AND METHOD USING A FLAT AMORPHOUS SILICON IMAGING PANEL

[75] Inventor: David L. Gilblom, Los Altos, Calif.

[73] Assignee: Varian Medical Systems, Inc., Palo Alto, Calif.

[21] Appl. No.: 09/262,397

[22] Filed: Mar. 4, 1999

Related U.S. Application Data

[63] Continuation of application No. 08/684,646, Jul. 19, 1996, abandoned.

[51] Int. Cl.$^7$ ............................................. G01T 1/24
[52] U.S. Cl. ................... 378/98.8; 378/98.8; 750/370.11
[58] Field of Search ................................. 378/98.8, 98.7, 378/108, 97; 250/370.11, 370.09, 370.06, 370.07, 367, 368

[56] References Cited

U.S. PATENT DOCUMENTS

| | | | |
|---|---|---|---|
| 5,194,736 | 3/1993 | Meulenbrugge et al. | 250/370.07 |
| 5,331,166 | 7/1994 | Yamamoto et al. | 250/370.11 |
| 5,608,774 | 3/1997 | Polichar et al. | 378/98.8 |

*Primary Examiner*—David P. Porta
*Attorney, Agent, or Firm*—Bradford L. Friedman; Hunter L. Auyang

[57] ABSTRACT

An x-ray imaging apparatus receives an image-carrying x-ray beam on a flat amorphous silicon imaging panel with a light detector unit disposed behind. The imaging panel is of a multi-layered structure having sequentially a light-blocking layer which is opaque to visible light but transmissive to x-rays, a converting layer of a phosphorescent material for converting x-rays incident thereon into visible light, and a two-dimensional array of photosensitive elements of an amorphous semiconductor material such as amorphous silicon, adapted to undergo a detectable change in electrical characteristic in response to impingement of light. The light detector unit may be a simple light detector for receiving the light emitted from the converting layer and passed through regions between neighboring pairs of the array of photosensitive elements. Since the energy of light thus detected is directly proportional to the total light energy emitted from the converting layer, the output signal from such a light detector unit can be conveniently used for the exposure control of the imaging panel.

13 Claims, 3 Drawing Sheets

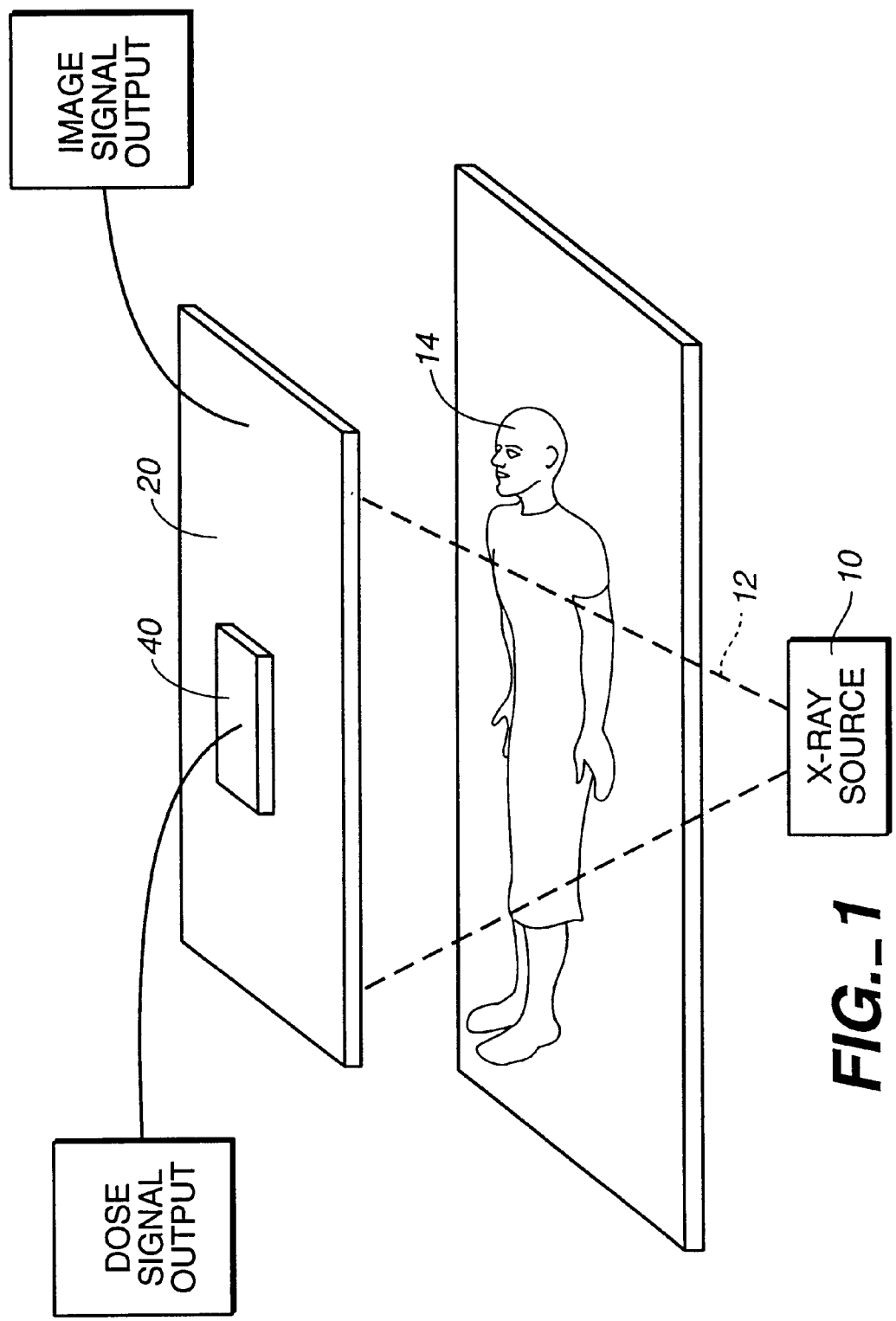

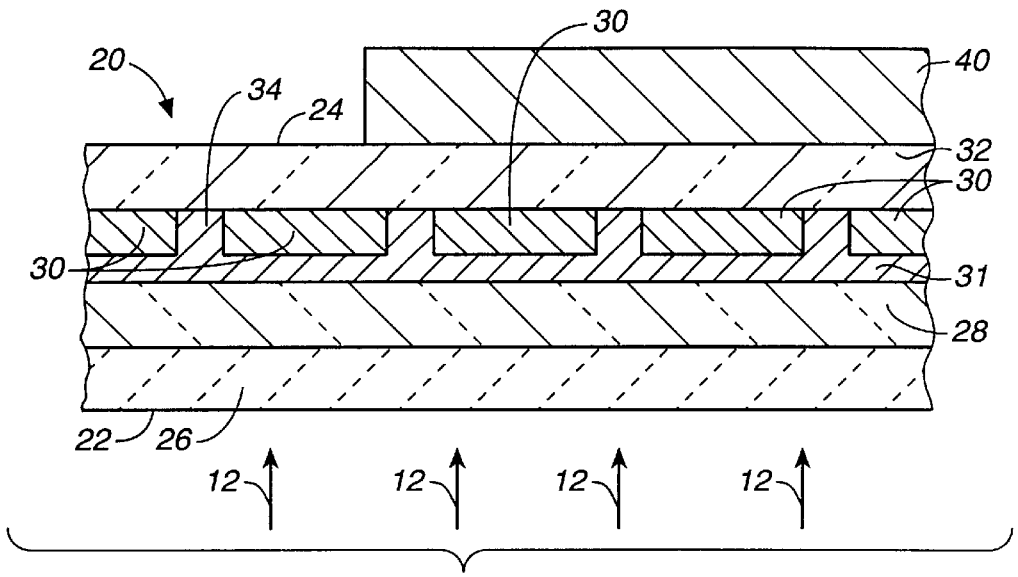
FIG._2
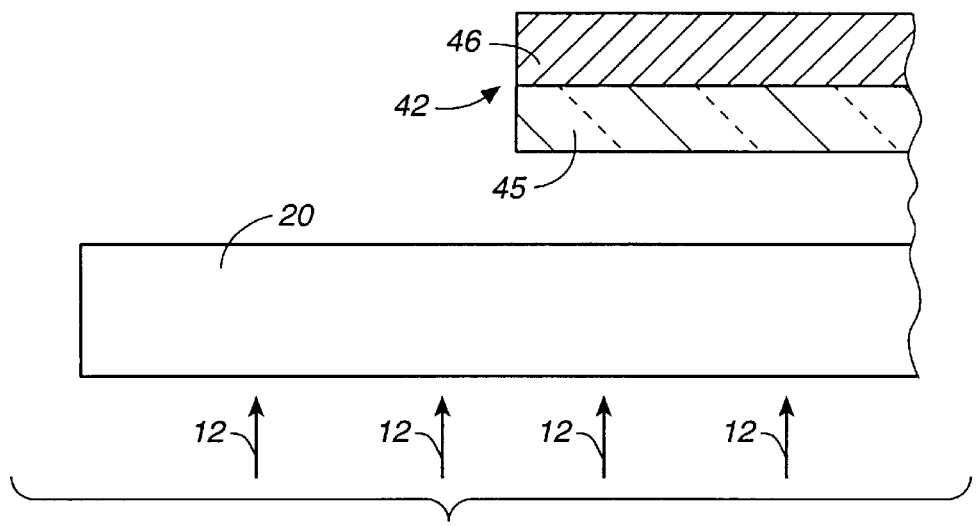
FIG._3
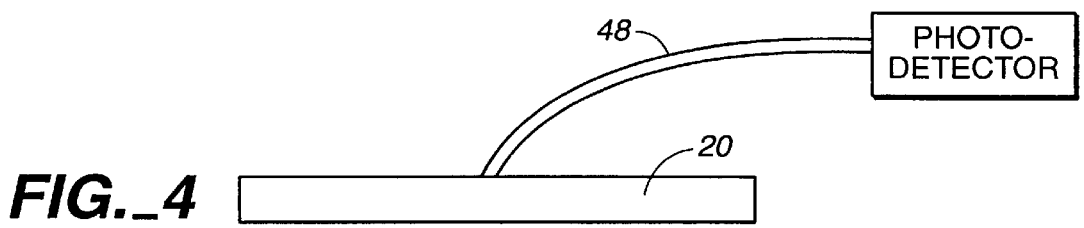
FIG._4

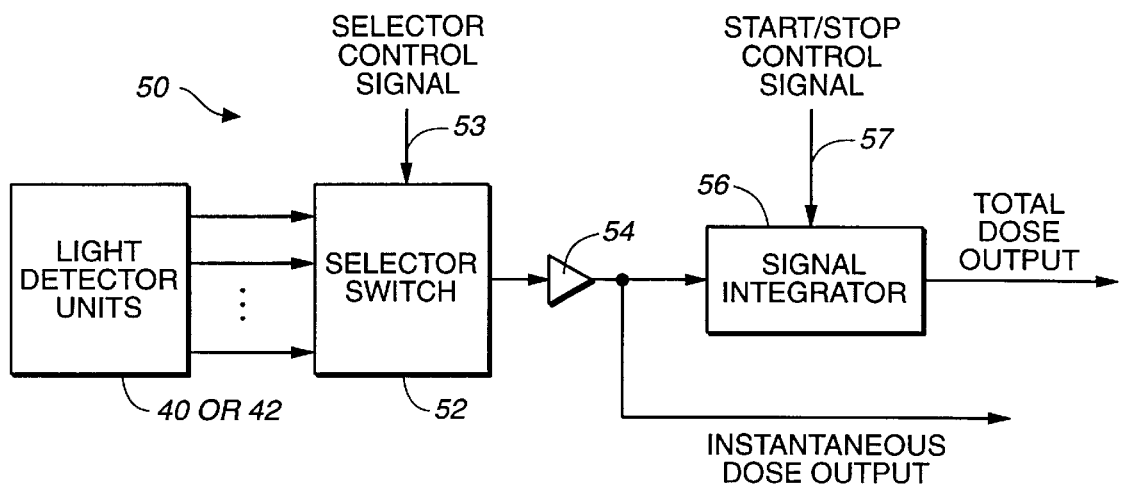
FIG._5
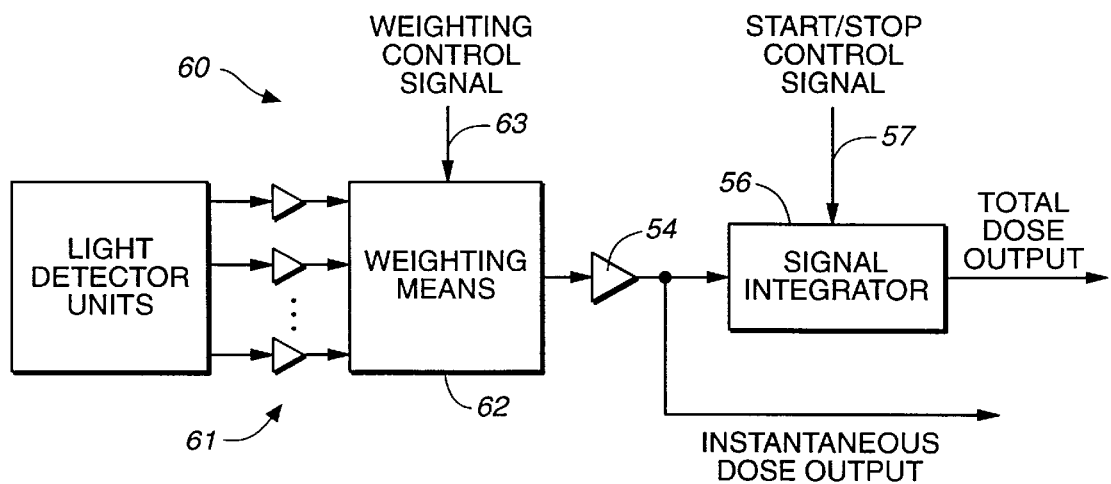
FIG._6

X-RAY IMAGING APPARATUS AND METHOD USING A FLAT AMORPHOUS SILICON IMAGING PANEL

CROSS-REFERENCE TO RELATED APPLICATIONS

This ia a continuation application of U.S. application Ser. No. 08/684,646 filed Jul. 19, 1996 now abandoned.

BACKGROUND OF THE INVENTION

This invention relates to an x-ray imaging apparatus and method using a flat imaging panel x-ray detector, and, more particularly, for such a panel imager having an array of light-sensitive elements comprising an amorphous semiconductor material such as amorphous silicon.

In view of many disadvantages associated with x-ray image intensifiers and film of conventional types such as large bulk, complexity and incorporation of moving parts, U.S. Pat. No. 4,672,454 disclosed a flat amorphous silicon imaging panel, comprising an array of light-sensitive elements, as small as about 90 microns to a side and formed from an deposited semiconductor material such as amorphous silicon. For using such an x-ray imager effectively, however, appropriate means are required for providing signals representing the x-ray dose being received. For single shot fluorography (wherein snapshots are taken with an electronic device), a signal representing total integrated dose will be required. For fluoroscopy (wherein an electronic device is used for continuous imaging), on the other hand, a signal representing the instantaneous x-ray flux will be needed. Although various apparatus for exposure control have been available for radiography (or direct imaging on a film) and fluoroscopy with x-ray intensifiers and television cameras, there have not been any suitable exposure control apparatus or method for use with a flat amorphous silicon imaging panel.

U.S. Pat. No. 3,995,161, for example, disclosed an x-ray exposure device using a multiple-section ion chamber with integrating capacitors to provide measures of dose in several areas of a film, but ion chambers are incompatible with amorphous silicon panels because they are too bulky and require high voltages which are likely to interfere with the panel operation. Moreover, they require power supplies which produce noise that is likely to harm the signal quality from the panel. U.S. Pat. No. 4,517,594 disclosed an x-ray installation whereby a small percentage of light outputted from an x-ray image intensifier is re-imaged on a segmented photodetector, but there is no x-ray intensifier with a flat panel, nor is there any means for re-imaging. U.S. Pat. No. 4,171,484 disclosed a direct view fluoroscopic imaging system with an image intensifier tube and a high-voltage bias supply therefor. Dose signals are derived from the variations in the output from a phosphor display screen. This scheme, however, admits no selection of image sampling area, and amorphous silicon panels have no equivalent power supply means. U.S. Pat. No. 4,679,217 disclosed a film cassette with small scintillating screens for producing light to be detected by photodetectors in the cassette holder. This scheme requires auxiliary equipment to produce electrical signals for use by a generator and therefore prevents utilization of the cassette exposure control in any film holder except those designed with the auxiliary electronics included. Moreover, the light output of the screens, if used with amorphous silicon panels, does not truly represent the panel exposure as it would when used with a film. U.S. Pat. No. 4,442,537 disclosed a system which uses a television camera to measure the output from an x-ray image intensifier. The output from the television camera tube is used to generate a regulating signal for the control unit. If such a video signal is generated from an amorphous panel, it will not be produced until scanning occurs, and it will be too late to control the x-ray dose for fluorographic use.

As illustrated by this limited number of examples given above, prior art exposure control apparatus cannot fulfil all requirements for size, power consumption and compatibility with the characteristics of amorphous silicon panels.

SUMMARY OF THE INVENTION

It is therefore an object of this invention to provide a convenient x-ray imaging apparatus and method for use with a flat imaging panel having an array of light-sensitive elements comprising an amorphous semiconductor material such as amorphous silicon.

An x-ray imaging apparatus embodying this invention, with which the above and other objects can be accomplished, may be characterized as comprising a flat amorphous silicon imaging panel and a light detector unit. The imaging panel is of a multi-layered structure having sequentially a light-blocking layer which is opaque to visible light but transmissive to x-rays, a converting layer of a phosphorescent material for converting x-rays incident thereon into visible light, and a two-dimensional array of photosensitive elements comprising an amorphous semiconductor material such as amorphous silicon, adapted to undergo a detectable change in electrical characteristic in response to impingement of light.

The light detector unit is disposed behind this imaging panel, opposite its energy-incident surface through which an image-carrying beam of x-rays is projected onto the panel. The light detector unit may be a simple light detector which will receive the light emitted from the converting layer and passed through regions between neighboring ones of the array of photosensitive elements. Since the energy of light thus detected is directly proportional to the total light energy emitted from the converting layer and, thus, received by the photosensitive elements, the output signal from such a light detector unit can be used conveniently for the exposure control of the imaging panel. The light detector unit may alternatively have its own converting layer covering its light-detecting layer such that the residual x-rays which have passed through the imaging panel without being absorbed by the converting layer can be detected. If two or more of such light detector units of either or both types are used, detection signals therefrom may be selectively used by means of a switching means or combined in a specified proportion by means of a weighting means for the purpose of exposure control.

BRIEF DESCRIPTION OF THE DRAWINGS

The accompanying drawings, which are incorporated in and form a part of this specification, illustrate embodiments of the invention and, together with the description serve to explain the principles of the invention. In the drawings:

FIG. 1 is a schematic of an x-ray imaging system incorporating an apparatus embodying this invention;

FIG. 2 is a schematic sectional view of a portion of x-ray imaging apparatus embodying this invention;

FIG. 3 is a schematic sectional view of a portion of another x-ray imaging apparatus embodying this invention;

FIG. 4 is a schematic sectional view of a portion of still another x-ray imaging apparatus embodying this invention;

FIG. 5 is a block diagram of an exposure control means associated with an x-ray imaging apparatus; and FIG. 6 is a block diagram of another exposure control means.

DETAILED DESCRIPTION OF THE INVENTION

An x-ray imaging system incorporating an apparatus which embodies this invention is schematically shown in FIG. 1. An x-ray generator tube 10 generates a beam of x-rays 12 adapted to pass through an object such as a patient to be x-rayed 14 and be received by a flat amorphous silicon imaging panel 20. As shown in FIG. 2, the panel 20 is of a multi-layered structure having an energy-incident surface 22, through which the image-carrying x-rays 12 are received, and a light-detecting surface 24 opposite thereto. Since aforementioned U.S. Pat. No. 4,672,454, herein incorporated by reference, describes a detector panel of this type in detail, FIG. 2 is intended to show the structure of the panel 20 only schematically as comprising a light-blocking layer 26, an x-ray scintillator layer 28 and a two-dimensional array of photosensitive elements 30 on a glass substrate 32, numeral 31 indicating an insulating layer filling the space in between. The light-blocking layer 26 is opaque to visible light but transmissive to x-rays and may comprise a thin layer of aluminum. The x-ray scintillating layer 28, which is continuous over the light-blocking layer 26, is of a phosphorescent material such as doped cesium iodide or gadolinium oxysulfide adapted to phosphoresce, when impinged upon by the x-rays 12, to convert the x-ray energy into light energy in a different range. The light-sensitive elements 30, which are themselves opaque, comprise an amorphous semiconductor alloy, and preferably amorphous silicon, capable of undergoing a detectable change in electrical characteristic in response to light received from the x-ray scintillating layer 28. Although not shown in FIG. 2 (but illustrated and explained in aforementioned U.S. Pat. No. 4,672,454), the panel 20 further includes means for individually detecting the electrical characteristic of these light-sensitive elements 30 and outputting signals indicative thereof (as shown schematically in FIG. 1). The light-sensitive elements 30 can be made to have dimensions of only about 90 microns on a side and hence are capable of representing an x-ray image with a high resolution. In order to increase absorption of light from the x-ray scintillating layer 28, light-transmissive regions 34 between neighboring pairs of the light-sensitive elements 30 are minimized but are yet adapted to transmit light from the x-ray scintillating layer 28 therethrough to the light-detecting surface 24.

For the purpose of automatic control of the x-ray dose from the x-ray generator tube 10, detecting means of different kinds may be used according to this invention, depending on the energy range expected and the transmission of the panel 20 to both x-rays and light.

FIG. 2 shows a simple light detector unit 40, which may be a silicon photodiode or phototransistor, an avalanche photodiode, or a miniature photo-multiplier, mounted behind the panel 20 (that is, either on its light-detecting surface 24 or sufficiently proximally thereto such that the separation therefrom will not significantly affect the amount of light collected from the x-ray scintillating layer 28). As described above, there are light-transmissive regions 34 between mutually adjacent ones of light-sensitive elements 30 through which visible light emitted from the x-ray scintillating layer 28 passes to reach the glass substrate 32 and received therethrough by the light detector unit 40.

Because the total light energy that is transmitted is in exact proportion of to the amount of light energy received and detected by the light detector unit 40, the proportionality can be easily calibrated preliminarily and the x-ray dose from the x-ray generator tube 10 can be easily determined from the charge read out from the light detector unit 40.

The type of detector unit to be used will depend on the amount of light which passes through the panel 20, depending on the panel transparency and x-ray dose rate. At high levels, a simple photodiode is suitable. At very low dose levels, an avalanche photodiode or even a photomultiplier might be needed. Because all of these devices are small compared to the sample area typically desired, some sort of shaped light collecting device ("a large area collector") may be needed. Examples of such a collecting device include a sheet of acrylic plastic (or polymethyl methacrylate).

Another type of detector unit 42 which may be used and illustrated in FIG. 3 is characterized as being adapted to detect x-rays rather than visible light, comprising a scintillator 45 in front of a light detector 46. The x-ray beam 12, incident onto the panel 20, is not totally absorbed by the x-ray scintillating layer 28 to be converted into light energy. A certain portion of the incident x-rays penetrates the panel 20 and reappears on the opposite side. The scintillator 45 is adapted to capture such left-over x-rays and the light energy thereby generated is received by the photosensor 46, which outputs a detection signal (not shown) indicative of the energy detected thereby. A detector unit of this type is less accurate because it measures the residual x-rays, rather than the absorbed x-rays directly, but this type of detector unit may be necessary where the transparency of the panel 20 is too low to permit direct detection of the light or where the scintillator does not produce sufficient light for proper operation of the detector. Given the voltage of the x-ray generator tube 10 and the knowledge of particular technique being used and the absorption characteristics of the panel 20, however, it is possible to obtain some approximate calibration, relating the detection signal with the x-ray dose. It is also to be noted that amorphous silicon panels are much more forgiving of exposure errors than films are. Because the residual x-rays passing through the panel 20 are generally still well collimated, unlike the phosphorescent light emitted from the x-ray scintillating layer 28, detector units of this kind for measuring left-over x-rays need not be mounted directly on the panel 20, as illustrated in FIG. 3.

Where the x-ray energy is relatively high (say, over 150 kev), it may be desirable to remove the light detector unit 40 from the x-ray beam to avoid long-term damage to the detector unit. In such a case, a bundle 48 of elongated non-coherent plastic fiber-optic material may be used, as shown in FIG. 4, to transmit the light from its light-receiving surface to the opposite end connected to the light detector unit 40. A radiation shield (not shown) may be provided, whenever necessary.

Although not separately illustrated, a fiber-optic bundles may be used for bringing together samples from remote areas on the light-detecting surface 24 to a single light detector unit, or a fiber-optic bundle may be used in connection with a large area collector.

In situations where it is desired to monitor multiple portions of the panel 20, say, for adapting to different anatomical examinations, a plurality of detector units may be provided, although not separately illustrated. Each of the plurality of such detector units may be adapted (being of the type shown in FIG. 2) to detect light from the x-ray scintillating layer 28 or (being of the type shown in FIG. 3)

to detect light from its own scintillator, or the left-over x-rays which have penetrated and passed the panel 20. In each of such applications, fiber-optic bundles may be used as shown in FIG. 4.

FIG. 5 shows an example of exposure control means 50 for controlling the x-ray generating tube 10 (shown in FIG. 1) according to the outputs from the light detector units 40 or 42, especially where a plurality of such detector units are used in the system. Output signals from the light detector units 40 or 42 are received by a selector switch 52, of which the function is to select one of the plurality of detector units in response to selector control signals 53 inputted by the user and to allow only the detection signal from the selected detector unit to pass therethrough. The detection signal which has been allowed to pass through the selector switch 52 is amplified by a signal amplifier 54. The amplified detection signal serves directly as the instantaneous dose output to control the x-ray dose from the x-ray generator tube 10 for online fluoroscopy. A portion of the amplified detection signal may be received by a signal integrator 56 to calculate the total dose represented by the received during a specified time interval between a start time and a stop time inputted through a start/stop control signal 57. The output from the signal integrator 56 serves as the total dose output to control the x-ray generator tube 10 for single-shot fluorography.

Such a control system with a switch suffices where only simple examinations are to be performed. Since each detector unit may include sampling of an extended area by use of light collectors and since there may be overlapping areas, a one-to-one anatomical programming method is possible. This scheme requires much advance planning, however, so a more complex method and scheme may be desirable.

FIG. 6 shows another example of exposure control means 60 which allows proportional mixing of the various signals as required by the anatomical configurations. Detection signals from the plurality of detector units are individually amplified by corresponding ones of signal amplifiers 61 and received by a weighting means 62 for proportionally mixing these individually amplified detection signals according to the weighting scheme communicated through weighting control signals 63 inputted by the user. In other regards, the control means 60 of FIG. 6 is the same as shown in FIG. 5 and hence these components that may be identical are indicated by the same numerals and not repetitively described.

With exposure control means as shown in FIG. 6, substantial additional flexibility can be provided in the control. An additional switch (not shown) may be provided to permit remote selection of the proportional or integrated signal outputs rather providing these on separate lines.

The invention has been described above with reference to only a limited number of examples, but these examples are intended to be merely illustrative, not as limiting. Many modifications and variations are possible within the scope of this invention. For example, the direct light detection schemes of this invention can be applied also to any light-detection applications for panels, not limited to those in which light is generated by an x-ray scintillator. In fact, any spatially distributed image-carrying form of electromagnetic or accelerated particle (such as electron) beam energy within an appropriate energy range can be used on an appropriate (such as solid state) energy converting means to generate light in another energy range. This invention has applications to a variety of scientific instruments in which optimum performance depends on reception of a sufficient amount of accumulated light before read-out. In summary, all such modifications and variations that may be apparent to a person skilled in the art are intended to be within the scope of this invention.

What is claimed is:

1. An imaging apparatus comprising an imaging panel with a multi-layered structure having an energy-incident surface and a light-detecting surface opposite to each other and a plurality of detector units with an energy-receiving surface disposed proximally to said light-detecting surface, said imaging panel including:

a light-blocking layer which is opaque to visible light and transmissive to an incident form of imageing energy projected on said energy-incident surface;

a converting layer between said light-blocking layer and said light-detecting surface for converting said incident form of image-carrying energy into light energy; and an array of photosensitive elements between said converting layer and said light-detecting surface, said elements undergoing a detectable change in electrical characteristic in response to impingement of light;

at least one of said detector units being adapted to receive directly from said imaging panel that portion of said incident form of said image-carrying energy not converted into light energy by said converting layer to provide a first output detection signal indicative of the energy received thereby; and at least another of said detector units being adapted to receive directly from said imaging panel said light from said converting layer passing between mutually neighboring pairs of said photosensitive elements to provide a second output detection signal indicative of the energy received thereby.

2. The imaging apparatus of claim 1 wherein said detector unit for detecting said incident form of said image-carrying energy comprises a light detector and a scintillator, said scintillator being adapted to convert said portion of said incident form of said image-carrying energy not converted by said converting layer into light energy, said light detector being attached to said scintillator and adapted to output said detection signal which is indicative of the light energy received thereby from said scintillator.

3. The imaging apparatus of claim 1 wherein said first output detection signal and said second output detection signal are selectively addressed by a switching means for the purpose of exposure control.

4. The imaging apparatus of claim 1 wherein said first output detection signal and said second output detection signal are combined in specific portions by use of a weighing means for the purpose of exposure control.

5. The imaging apparatus of claim 1 further comprising an exposure control means for outputting instantaneous dose signals indicative of energy being received instantaneously by said imaging panel.

6. The imaging apparatus of claim 5 wherein said exposure control means include a selecting means for selecting one of said plurality of detector units and outputting said instantaneous dose signal from said selected detector unit.

7. The imaging apparatus of claim 5 wherein said exposure control means include a weighting means for proportionally mixing the detection signals from said detector units according to a weighting scheme inputted thereto through weighting control signals.

8. The imaging apparatus of claim 6 wherein said exposure control means further includes an integrator for accumulating the instantaneous dose signals over a specified period of time and thereby outputting a total dose signal indicative of the total dose of energy received by said selected detector unit.

9. The imaging apparatus of claim 5 wherein said exposure control means further includes an integrator for accumulating the instantaneous dose signals over a specified period of time and thereby outputting a total dose signal indicative of the total dose of energy received by a combination of said detector units according to said weighting system.

10. An imaging method comprising the steps of:
causing a selected form of energy to penetrate and pass through a target object to thereby form image-carrying energy and projecting said image-carrying energy onto an energy-incident surface of an imaging panel with a multi-layered structure;
causing said image-carrying energy to pass through a light-blocking layer of said panel;
thereafter converting said image-carrying energy into light through a converting layer of said panel, said panel having an array of photosensitive elements behind said converting layer, said elements being capable of undergoing a detectable change in electrical characteristic in response to impingement of light;
detecting said change to obtain an image of said target object;
using a first detector unit outside a light-detecting surface of said imaging panel which is opposite said energy-incident surface to detect light from said converting layer passing between mutually neighboring pairs of said photosensitive elements and a second detector unit to detect said image-carrying energy of said incident form which has penetrated and passed through said imaging panel; and
outputting a combined detection signal indicative of the energy received by said imaging panel.

11. The method of claim 10 wherein said selected form of energy is a beam of x-rays.

12. The method of claim 10 wherein said first and second detector units are disposed at different positions, said method further comprising the steps of:
inputting a weighting scheme;
proportionally mixing the detection signals from said detector units according to said weighting scheme to thereby obtain a mixed detection signal; and
outputting an instantaneous dose signal on the basis of said mixed detection signal.

13. The method of claim 10 further comprising the step of accumulating the instantaneous dose signals over a specified period of time to obtain a total dose signal indicative of the total dose of energy received during said period of time by said detector units.

* * * * *